United States Patent [19]

Freedman et al.

[11] Patent Number: 4,634,675
[45] Date of Patent: Jan. 6, 1987

[54] AGITATOR FOR A FERMENTATION AND TISSUE CULTURING VESSEL

[75] Inventors: David Freedman, Highland Pk.; Zheng Zhenbin, New Brunswick, both of N.J.

[73] Assignee: New Brunswick Scientific Co., Inc., Edison, N.J.

[21] Appl. No.: 566,628

[22] Filed: Dec. 29, 1983

[51] Int. Cl.$^4$ ............................................. C12M 3/02
[52] U.S. Cl. .................................. 435/286; 435/284; 435/316; 366/305
[58] Field of Search ................. 435/286, 316; 366/305

[56] References Cited

U.S. PATENT DOCUMENTS 4,178,209  12/1979  Tolbert et al. ..................... 435/286

FOREIGN PATENT DOCUMENTS 1295990  12/1962  France .............................. 366/305
 688308   3/1953  United Kingdom .
 745457   2/1956  United Kingdom .
 832526   4/1960  United Kingdom .
1173455  12/1969  United Kingdom .
2106540A  4/1983  United Kingdom .

OTHER PUBLICATIONS

Microcarrier Cell Culture Principles & Methods, pub. by Pharmacia Fine Chemicals, pp. 4-12, 34-42 and 45-48, Dec. 1981-1.

Primary Examiner—Sam Rosen
Attorney, Agent, or Firm—Blum, Kaplan, Friedman, Silberman & Beran

[57] ABSTRACT

An improved agitator for use with a fermentation and tissue culturing vessel acting as a microcarrier culture vessel is provided. The agitator includes a hollow body assembly having an open end and a closed end and at least one tubulation communicating with the hollow body assembly at a location spaced from the open end thereof, the tubulation having an exit opening oriented such that movement of the agitator and the tubulation causes a suction or draft at the exit opening to cause flow of fluid from the open end of the hollow body assembly through the hollow body assembly and out through the tubulation exit opening. In this way, a microcarrier cell culture may be stirred in a smooth and non-erratic way thereby minimizing the detachment of the rounded growth cells from the microcarriers.

16 Claims, 5 Drawing Figures

FIG. 3
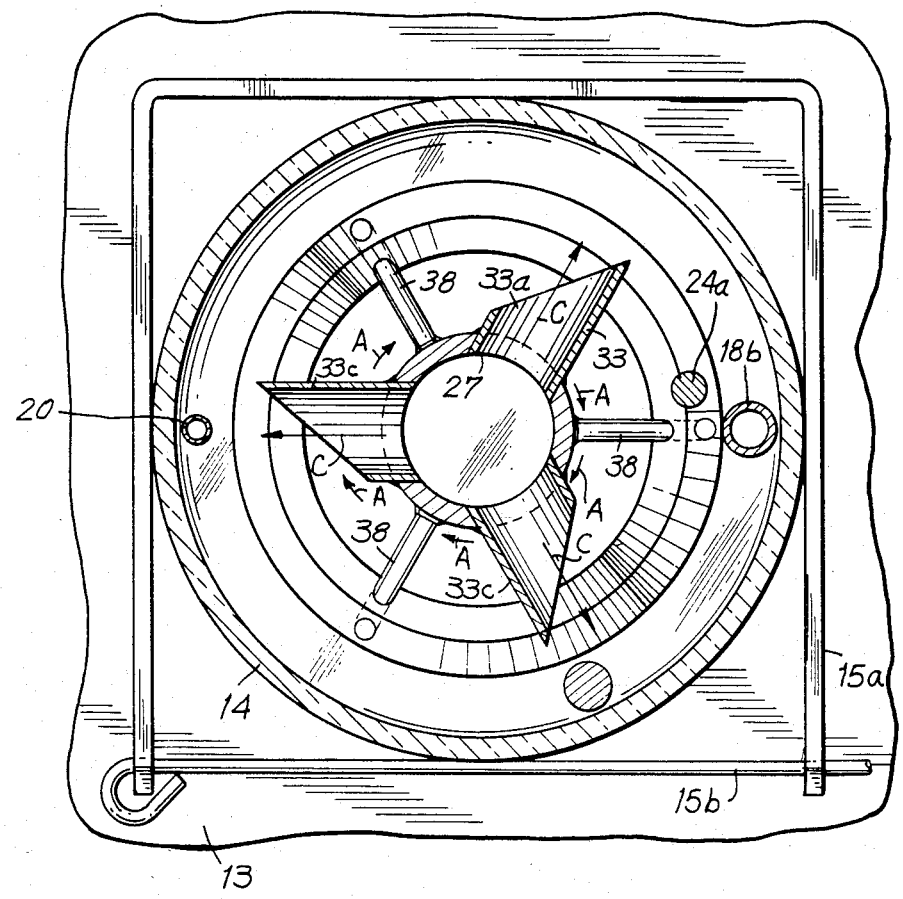
FIG. 4
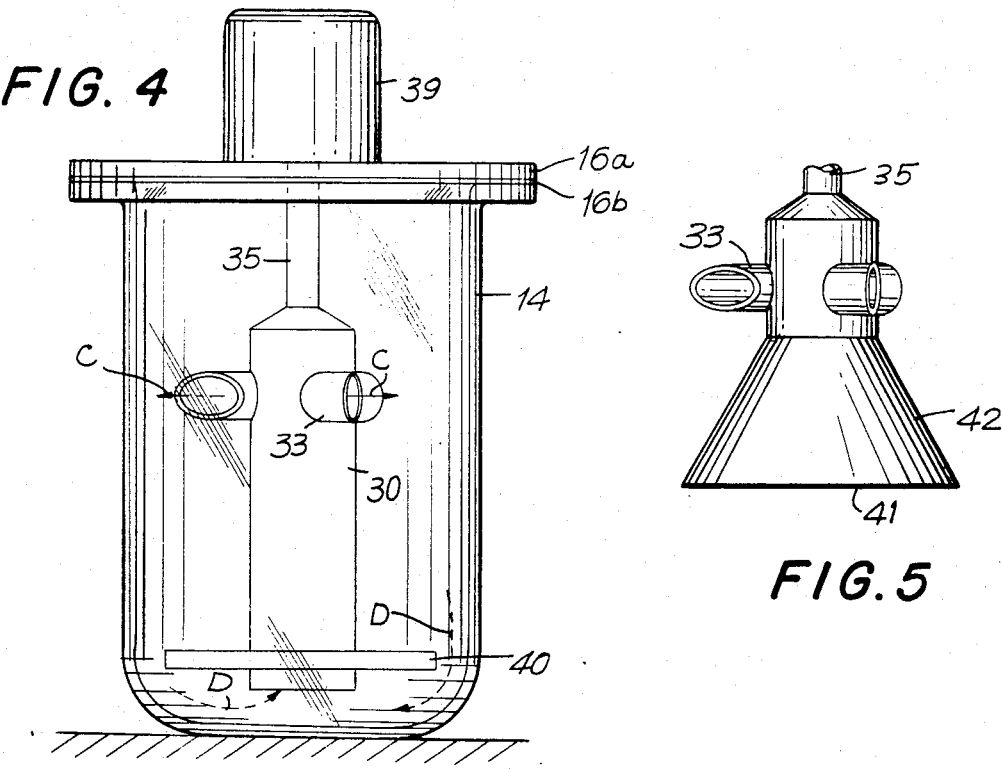
FIG. 5

AGITATOR FOR A FERMENTATION AND TISSUE CULTURING VESSEL

BACKGROUND OF THE INVENTION

This invention relates generally to an agitator for a fermentation and tissue culturing vessel and more particularly to an improved agitator for a fermentation and tissue culturing vessel wherein said fermentation and tissue culturing vessel is utilized as a microcarrier culture vessel.

The use of cell culturing techniques are widely known, and are vital to the study of animal cell structure and for the production of important medical material such as hormones, enzymes, antibodies, vaccines, etc. When using tissue and microcarrier cell culturing techniques, the cells are ultra-fragile in nature, and easily damaged during growth. The culturing of anchorage-dependent cells has proved particularly difficult and the use of microcarriers for this purpose has been developed. In microcarrier cultures, cells are grown as single layers on a surface of microcarriers, generally small spheres, which are in turn suspended in a culture medium by gentle agitation. A detailed description of microcarrier cell culture principles and methods and prior art systems of agitation may be found in the book "Microcarriers Cell Culture: Principles and Methods", Pharmacia Fine Chemicals, Sweden, December 1981.

As noted in the reference above, the highest yield for microcarrier cultures are obtained when the microcarriers are evenly suspended in the culture medium and are given the possibility for adequate exchange of gases with said culture medium. Erratic agitation or stirring motions must be avoided since these may lead to the detachment of the rounded mitotic cells from the microcarriers. For this reason, it is important to avoid exposing the culture medium and microcarriers to vibrations. On the other hand, agitation or stirring is essential to ensure that the entire surface of the microcarriers is available for cell growth, to create a homogeneous culture environment, to avoid aggregation of microcarriers and to facilitate the exchange of gases between the culture headspace and the medium.

A number of techniques have been utilized to provide suspension and aeration for the microcarriers and cells including spinner and rod-stirred vessels, the use of roller bottles, the use of rocking bottles, and the use of air-lift and fluid-lift culture medium systems. Efforts to improve agitation have included use of ball-tipped stirring rods fixed at one end and displaced in a circular path at the other end about a projection in the base of the vessel, and the use of paddle and plunger shaped impellers.

However, these systems have proven to be less than satisfactory, especially when employed in large scale commercial fermentation and tissue culturing assemblies, and are limited in the degree of control over the speed and force of microcarrier movement and aeration.

Accordingly, it is desirable to provide an agitator for use with a fermentation and tissue culturing vessel which is capable of keeping microcarrier cell cultures suspended to allow for exchange of gases, while minimizing the detachment of the growing cells from the microcarriers.

SUMMARY OF THE INVENTION

Generally speaking, in accordance with the invention, an improved agitator for a fermentation and tissue culturing vessel is provided. The agitator utilizes a hollow body assembly having a first open end and a second closed end. At least one tubulation is coupled to an opening in the hollow body assembly in a region spaced from the first open end thereof to allow a flow to pass from the opened first end of said hollow body assembly toward the closed second end thereof and out through said tubulation. The outer end of said tubulation defines an exit opening positioned so that when the hollow body assembly is rotated about a longitudinal axis in the fermentation and tissue culturing vessel a suction force is created at the first open end. The hollow body assembly is preferably supported vertically in the vessel with the first open end in spaced facing relation to the bottom thereof, such that fluid will be drawn into the first open end of said hollow body assembly and, will be moved through said hollow body assembly, through said tubulation and out of said first end of said tubulation. In this way a gentle flow is provided from the bottom of the fermentation and tissue culturing vessel towards the top of the fermentation and tissue culturing vessel allowing the microcarrier cultures to remain evenly suspended in solution and also permitting the exchange of gases.

Specifically, the exit opening of the tubulation faces essentially in a direction opposite to the direction of rotation of the hollow body assembly. A plurality of tubulations may be provided. The tubulations may be coupled to openings in the side wall of the hollow body assembly, which may be cylindrical in shape in the region adjacent to the second closed end thereof.

The hollow body assembly may be mounted for free rotation in the vessel and may support a permanent magnet for coupling to a magnetic drive outside the vessel to effect rotation. The magnet may be an annular magnet supported in the region adjacent said first open end of said hollow body assembly. A laterally extending plate may be supported adjacent the first open end of the hollow body assembly for guiding flow of fluid in the vessel along the bottom thereof.

Accordingly, it is an object of the invention to provide an improved agitator for a fermentation and tissue culturing vessel.

Another object of the invention is to provide an improved agitator for a fermentation and tissue culturing vessel which is used as a microcarrier culture vessel.

A further object of the invention is to provide an improved agitator for a fermentation and tissue culturing vessel used as a microcarrier culture vessel wherein the agitator provides for the suspension and aeration of cells formed on microcarriers while minimizing the detachment of said cells from said microcarriers.

Still other objects and advantages of the invention will in part be obvious and will in part be apparent from the specification.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 is a cross-sectional view taken along line 3—3 of FIG. 2;

FIG. 4 is a plan view of an agitator using an alternate driving method made according to the invention; and FIG. 5 is a plan view of an alternate configuration of the hollow body assembly in accordance with the invention.

DETAILED DESCRIPTION OF THE PREFERRED EMBODIMENTS

Figure 1:
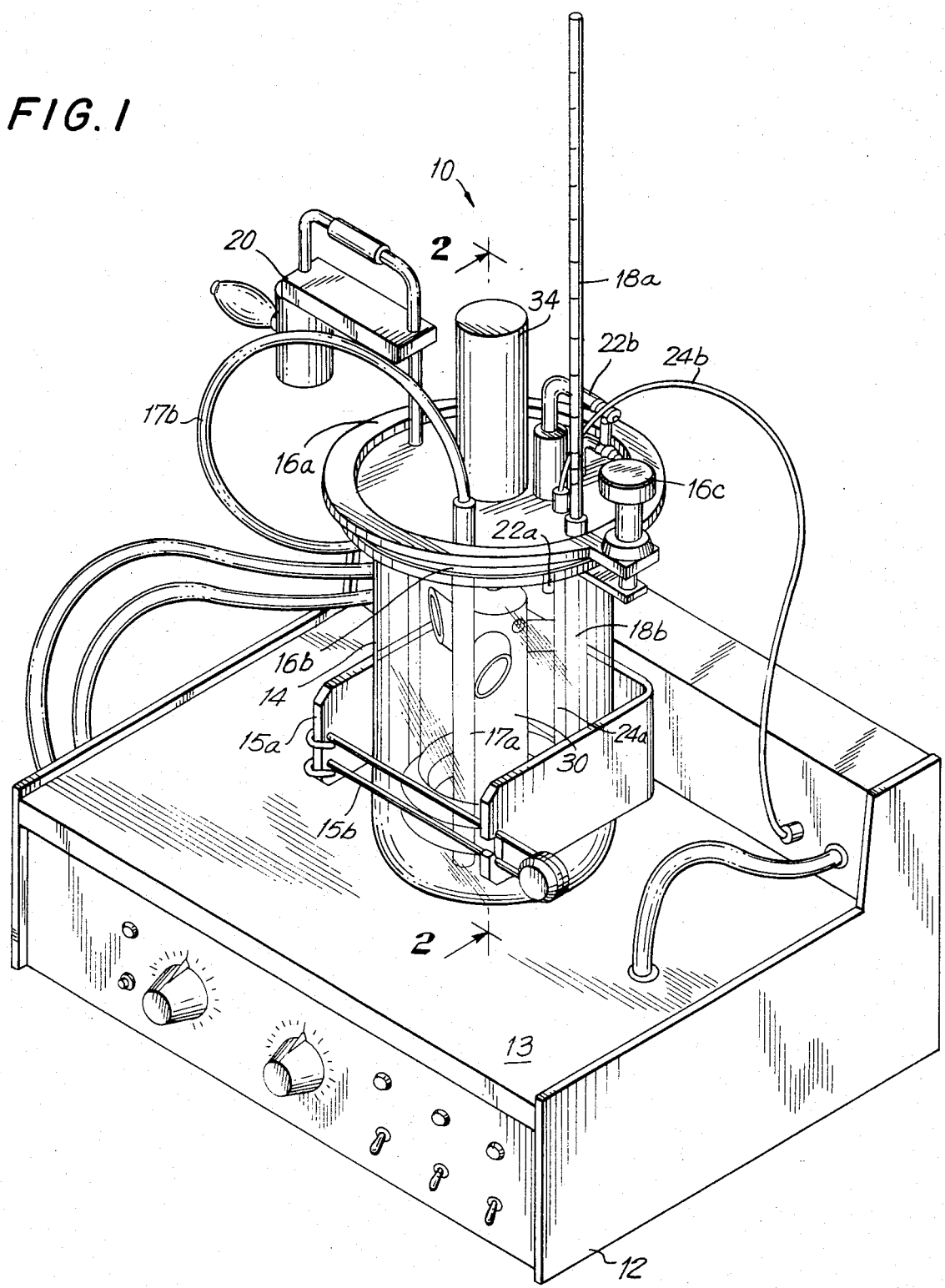
FIG. 1 is a perspective view of a laboratory fermenter utilizing an agitator of the invention.
Figure 2:
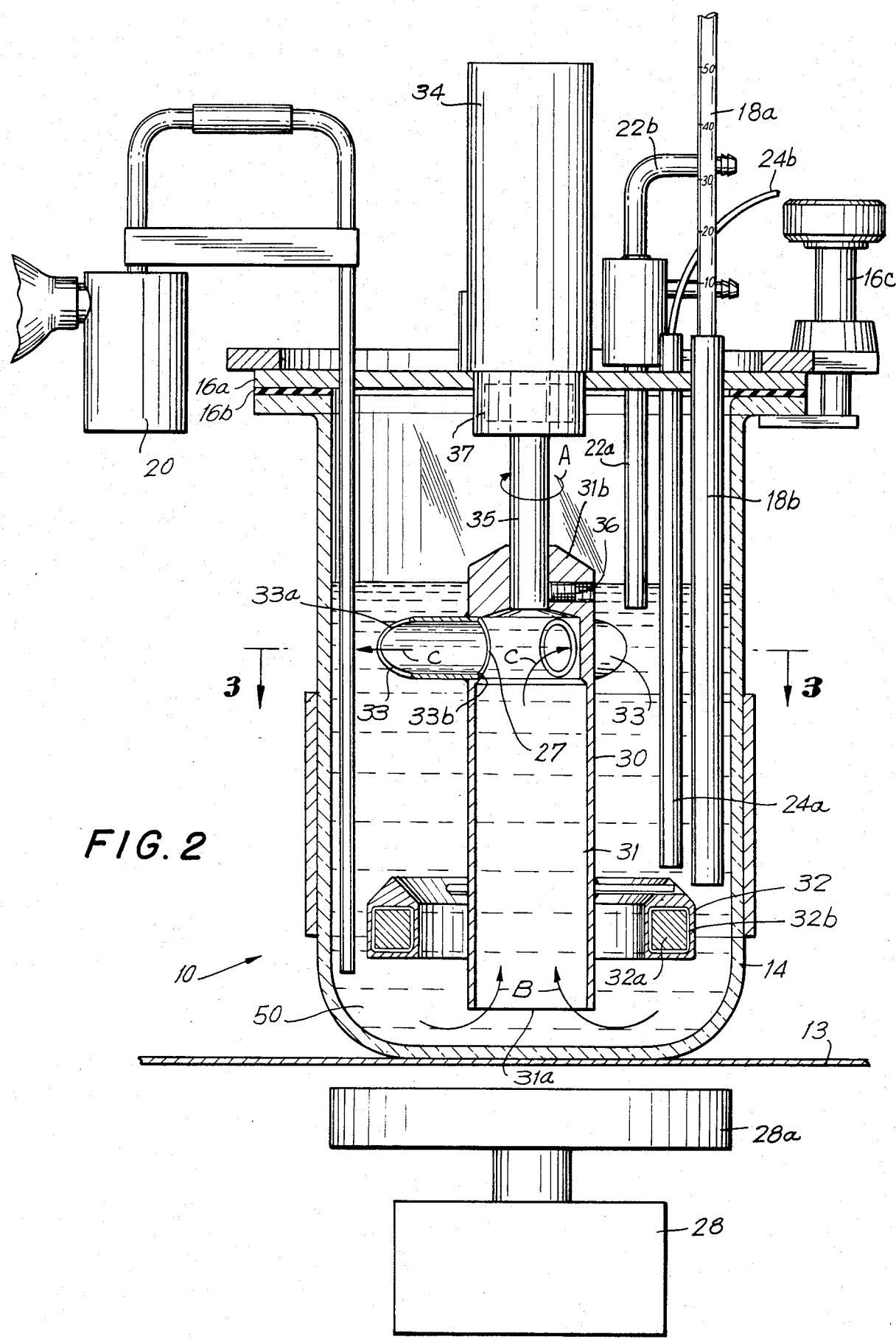
FIG. 2 is a cross-sectional view taken along line 2—2 of FIG. 1.

Referring now to FIGS. 1-3, one type of laboratory fermenter 10 is shown, incorporating the agitator in accordance with the invention, by way of example. The fermenter includes a controller 12 which contains the apparatus necessary to operate the fermenter and may in addition contain a magnet drive motor assembly 28 (FIG. 2). A fermentation and tissue culturing vessel 14 is positioned on top surface 13 of controller 12 and connections are made thereto for monitoring and controlling the cell growth process. Vessel 14 is held in position by U-shaped bracket 15a and releasable bail 15b. Fermentation vessel 14 is sealed through the use of a vessel cap 16a sealed against a top flange of the vessel through gasket 16b and held in place by clamp 16c. Fermentation vessel 14 is provided with a heater 17a and heater control line 17b which are used to raise the temperature of the contents of fermentation and tissue culturing vessel 14. Fermentation vessel 14 is also provided with a cold finger 22a and cold connection line 22b which allows the temperature of the contents of the fermentation and tissue culturing vessel 14 to be lowered. A thermometer 18a is mounted in a cylindrical tube 18b mounted in the vessel to indicate the temperature of the contents of the fermentation and tissue culturing vessel. The fermentation and tissue culturing vessel 14 also includes a sampler assembly 20 which may be used to remove a portion of the contents of the fermentation and tissue culturing vessel without disturbing operation of the fermenter 10.

The fermenter vessel 14 is also provided with a dissolved oxygen probe 24a having an output cable 24b, used for measuring the percentage of oxygen contained in the fermentation and tissue culturing vessel medium.

The various sensors and control devices depicted are examples of the many types of such devices which may be included in a fermentation and tissue culturing vessel and do not form a part of the invention. Means may be provided for defoaming, addition of medium and other functions if desired.

An agitator 30 in accordance with the invention is supported on cover 16a. The agitator includes a cylindrical hollow body assembly 31 having a first open end 31a and a second closed end 31b. The hollow body assembly incorporates tubulations 33 which project laterally from said hollow body assembly proximate to the second end 31b of said assembly 31. Said tubulations 33 are hollow, and include a first end defining an exit opening 33a and a second end 33b. Said second end 33b of each said tubulation 33 is connected to said hollow body assembly 31 at an opening 27 in the cylindrical wall of the hollow body assembly so that flow through open end 31a of the hollow body assembly exits through openings 27 and continues through the tubulations and out exit openings 33a. The exit opening 33a of each tubulation 33 is constructed so as to essentially face in a direction opposite to the direction of rotation of agitator 30 illustrated by arrow A of FIGS. 2 and 3. In operation, when agitator 30 is rotated about its longitudinal axis in the direction of arrow A such that a closed face 33c of each tubulation 33 lead the movement of the tubulation, a suction or draft if created within the hollow body assembly 31 and the tubulation 33. This will cause the movement of the fluid material 50 in the fermentation and tissue culturing vessel 14 to move into the opening 31a of the hollow body assembly 31 in the direction of arrows B (FIG. 2) and out of the opening 33a of the tubulations 33 in the direction of arrows C (FIGS. 2 and 3). If the level of the fluid in the fermentation and tissue culturing vessel is above the tubulations, a circulation will be created whereby material is taken from th bottom of the fermentation and tissue culturing vessel and brought to the top of the fermentation and tissue culturing vessel. This will allow for the movement and aeration of the microcarrier cell structures suspended in the fluid while minimizing detachment of the cells from the microcarriers.

Agitator 30 is mounted on shaft 35 by means of set screw 36, shaft 35 in turn is rotatably supported by bearing assembly 34, which includes bearings 37 (FIG. 2). An annular driven magnet assembly 32 is affixed proximate to the first end 31a of hollow body assembly 31 by means of rods 38. Driven magnet assembly 32 includes an annular permanent magnet 32a surrounded and supported by a protective sheath 32b to which rods 38 are secured. When magnet 28a of the magnetic drive motor 28 rotates it causes the driven magnet assembly 32 to rotate as well, thereby turning the agitator 30 and shaft 35 on the axis defined by said shaft. A conventional magnetic drive motor including a driving magnet 28a is mounted below surface 13 of controller 12 in registration with vessel 14. When utilizing this method, no direct physical connection between the drive motor and the agitator is required. Further, the driven magnet assembly aids in spreading the flow path on the bottom of vessel 14 to and in preventing accumulation of microcarriers at the periphery of the bottom.

Referring now to FIG. 4, an alternate embodiment is shown wherein the agitator bearing assembly is replaced with a direct drive motor assembly 39, so that agitator 30 is directly driven without magnets. A laterally extending plate 40 is mounted adjacent the first open end of hollow body assembly 31 to spread the flow currents set up by agitator 30 in the bottom region of vessel 14 as illustrated by arrows D. In operation of the fermenter as a microcarrier culture vessel, the shape of the vessel is usually chosen to prevent sedementation of microcarriers in any part of the culture vessel, namely with slightly rounded bases. The embodiment of FIG. 4 permits use of an essentially flat bottomed vessel.

As illustrated in the drawings, the agitator in accordance with the invention utilizes a plurality of tubulations. As shown, three tubulations are affixed to the hollow body assembly. However, it is noted that a greater or lesser number of tubulations may be provided as long as there is at least one. The number of tubulations and the general configuration will control the speed and force of the suction or draft. This will also be affected by the speed at which the agitator is turned.

Additionally, while the agitator of the invention is shown in operation in a desk top laboratory fermenter, its size may be scaled so that it might function in commercial fermentation and tissue culturing applications as well. One advantage of the agitator in accordance with the invention is the ability to scale it upward for larger vessel applications. While particularly useful in microcarrier cell growth applications, the agitator in accordance with the invention may be used for all agitator and fermentation and tissue culturing application. While the agitator 30 is shown top mounted, bottom mounting to a motor shaft journalled through the bottom of a vessel is also possible.

While a particular shape of tubulation is depicted, other shapes may be used so long as the exit opening thereof essentially faces in the direction opposite to the direction of rotation of the agitator. Even a scoop-shaped tubulation with little or no wall on the side opposite to the direction of rotation of the agitator can function in certain embodiments. Hollow body assembly 31 may be cone-shapd with an enlarged first open end 41, as illustrated by the hollow body assembly 42 of FIG. 5.

It will thus be seen that the objects set forth above and those made apparent from the preceding description are effectively attained, and since certain changes may be made in the above constructions without departing from the spirit and scope of the invention, it is intended that all matter contained in the above description or shown in the accompanying drawings shall be interpreted and illustrative and not in a limiting sense.

It is also to be understood that the following claims are intended to cover all of the generic and specific features in the invention herein described and all the statements of the scope of the invention which, as a matter of language, might be said to fall therebetween.

What is claimed is:

1. An agitator for use with a fermentation and tissue culturing vessel which comprises:
    displaceably mountable hollow body means having a lower open end for placement facing a bottom surface of said vessel and an upper closed end and formed with at least one side opening at a point spaced from said open end; and
    at least one tubulation means affixed to said hollow body means at said side opening in the hollow body means, said tubulation means having at least an input opening in registration with the side opening in the hollow body means and an exit opening, the exit opening being oriented so that when said hollow body and tubulation means are displaced a suction force is generated at said tubulation means exit opening operating to draw fluid into said hollow body means at its lower open end, out of said hollow body means through the side opening into the tubulation means, and through said tubulation means to said exit opening.

2. An agitator for use with a fermentation and tissue culturing vessel as claimed in claim 1, further comprising driving means for causing said hollow body means to be displaced in rotation.

3. The agitator for use with a fermentation and tissue culturing vessel, as claimed in claim 2, wherein said hollow body means has a side wall and an end wall, said side opening being formed in the side wall thereof, said hollow body means being rotatable about the axis of said side wall passing through said lower open end.

4. The agitator for use with a fermentation and tissue culturing vessel as claimed in claim 3, wherein said tubulation means essentially projects laterally from said side wall, said exit opening essentially facing in a direction opposite to the direction of rotation of said hollow body means.

5. The agitator for use with a fermentation and tissue culturing vessel as claimed in claim 4, wherein said tubulation means and the associated side opening on said hollow body means are positioned in the region adjacent to said end wall defining said upper closed end.

6. The agitator for use with a fermentation and tissue culturing vessel as claimed in claim 5, including a plurality of said tubulation means each projecting from said hollow body means at a side opening therein.

7. The agitator as claimed in claim 3, wherein said hollow body means side wall is essentially cylindrical.

8. The agitator for use with a fermentation and tissue culturing vessel as claimed in claim 3, wherein said hollow body means side wall is at least in part conical with said lower first open end being larger in diameter than said upper closed end.

9. The agitator for use with a fermentation and tissue culturing vessel as claimed in claim 2, wherein said driving means includes a driven magnet assembly coupled to said hollow body means proximate to said lower open end of said hollow body assembly and means for freely rotatably supporting said hollow body means, whereby said driven magnet assembly may be rotatably driven by a magnetic drive means outside said vessel without direct physical connection between said motor means and said agitator.

10. The agitator for use with a fermentation and tissue culturing vessel as claimed in claim 9, wherein said hollow body means includes a side wall defining said lower open end so that said lower open end is positioned in spaced facing relation to the bottom of said vessel, said magnetic driven means including a permanent magnet dimensioned to surround said side wall in spaced relation thereto at the region adjacent said lower open end.

11. The agitator for use with a fermentation and tissue culturing vessel as claimed in claim 2, wherein said drive means comprises a drive motor means coupled to said hollow body assembly proximate to said upper closed end of said hollow body assembly to provide a direct connection between said driving means and said agitator.

12. The agitator for use with a fermentation and tissue culturing vessel as claimed in claim 3 including a plate means extending laterally from said side wall proximate to said lower open end, said lower open end being positioned in spaced facing relation to the bottom of said vessel.

13. The agitator for use with a fermentation and tissue culturing vessel as claimed in claim 12, wherein said plate means is dimensioned so that the periphery thereof is in spaced relation to the side wall of said vessel so that said suction force causes the flow of fluid along said side wall past said plate and along the bottom of said vessel to said hollow body means lower open end.

14. The agitator for use with a fermentation and tissue culturing vessel as claimed in claim 2, in combination with a microcarrier culture field.

15. The agitator for use with a fermentation and tissue culturing vessel as claimed in claim 1, wherein said side opening is located closer to said upper closed end than to said lower open end.

16. The agitator for use with a fermentation and tissue culturing vessel as claimed in claim 1, wherein said side opening is located proximate said upper closed end.

* * * * *